US008257301B2

(12) United States Patent
Buisson (10) Patent No.: US 8,257,301 B2
(45) Date of Patent: Sep. 4, 2012

(54) DEVICE FOR ADMINISTERING SEVERAL LIQUID MEDICINES TO A PATIENT

(76) Inventor: Philippe Buisson, Toussieu (FR)

( * ) Notice: Subject to any disclaimer, the term of this patent is extended or adjusted under 35 U.S.C. 154(b) by 377 days.

(21) Appl. No.: 12/269,426

(22) Filed: Nov. 12, 2008

(65) Prior Publication Data

US 2009/0137951 A1 May 28, 2009

Related U.S. Application Data

(60) Provisional application No. 60/988,452, filed on Nov. 16, 2007.

(51) Int. Cl.
*A61M 37/00* (2006.01)
*A61M 31/00* (2006.01)
*A61F 11/00* (2006.01)
*A61F 2/06* (2006.01)

(52) U.S. Cl. .......... 604/87; 604/500; 606/108; 623/1.11

(58) Field of Classification Search .................. 604/500, 604/87; 606/108; 623/1.11
See application file for complete search history.

(56) References Cited

U.S. PATENT DOCUMENTS

| 4,447,230 | A | 5/1984 | Gula et al. | |
|---|---|---|---|---|
| 4,915,688 | A * | 4/1990 | Bischof et al. | 604/83 |
| 7,566,321 | B2 * | 7/2009 | Gumb et al. | 604/191 |
| 2001/0046181 | A1 * | 11/2001 | Paetow et al. | 366/177.1 |
| 2006/0089604 | A1 | 4/2006 | Guerrero | |
| 2007/0135765 | A1 * | 6/2007 | Miller et al. | 604/131 |
| 2007/0215209 | A1 * | 9/2007 | Street et al. | 137/263 |
| 2008/0045925 | A1 * | 2/2008 | Stepovich et al. | 604/518 |
| 2008/0221602 | A1 * | 9/2008 | Kuehner et al. | 606/167 |
| 2008/0271796 | A1 * | 11/2008 | Neumann et al. | 137/606 |

FOREIGN PATENT DOCUMENTS

| EP | 0442135 | 8/1991 |
|---|---|---|
| GB | 2414678 | 12/2005 |
| WO | 9406489 | 3/1994 |
| WO | 2004045704 | 6/2004 |

\* cited by examiner

*Primary Examiner* — Nicholas Lucchesi
*Assistant Examiner* — Ian Holloway
(74) *Attorney, Agent, or Firm* — Cantor Colburn LLP (57) ABSTRACT

This device comprises a tube (22) containing several substantially parallel channels extending along the entire length of tube of which one end, referred to as distal, is connected with a connection element to the patient, thereby forming a mixing chamber for the various liquids, and of which the other end, referred to as proximal, is connected to a housing (3) provided with connection means (9) for several containers each containing a liquid, wherein the housing has liquid delivery lines (7), wherein each delivery line (7) is intended to be connected to a container and to a channel of the tube (22) respectively. At least one delivery line (7) of the housing is provided with a check valve (12) intended to prevent the passage of liquid from the channel of the corresponding tube into the corresponding container.

17 Claims, 7 Drawing Sheets

DEVICE FOR ADMINISTERING SEVERAL LIQUID MEDICINES TO A PATIENT

This invention relates to a device for delivering several medical treatment liquids to a human or animal patient.

Document WO 2004/045704 teaches a device for delivering several medical treatment liquids to a patient, comprising a tube containing several substantially parallel channels extending along the entire tube of which one end, referred to as distal, is connected with a connection element to the patient, thereby forming a mixing chamber for the various liquids, and of which the other end, referred to as proximal, is connected to a housing provided with connection means for several containers each containing a liquid, wherein each delivery line is intended to be connected to a container or to a channel of the tube respectively.

In the case if, for example, various gravity perfusions are connected to the housing of that type of delivery device or if gravity infusions or positive pressure infusions controlled, for example, by means of pump syringes, are connected to the housing of said device, an amount of liquid may, due to the differences in pressure present in the various containers, leak out from the mixing chamber into one or more containers.

The result is a mixture of various liquids in certain containers thereby causing uncertainty about the actual quantity of each liquid being delivered to the patient, which can give rise to an incorrect treatment of the patient.

Likewise, due to the differences in pressure between venous pressure and pressures present in the various containers, blood may also leak out into one or several containers thereby preventing suitable delivery of the various liquids.

Consequently, the delivery device described in document WO 2004/045704 does not suitably deliver the medical treatment liquids contained in the various containers connected to that device.

The basic technical problem that the invention thus addresses consists of how to provide a delivery device having a simple structure for delivering several medical treatment liquids to a patient, while at the same time ensuring proper delivery of the liquids contained in the various containers connected to the device and ensuring proper patient treatment.

To this effect, the present invention relates to a delivery device of the aforementioned type, characterized in that at least one delivery line of the housing is provided with a check valve suitable for the passage of liquid only from the corresponding container towards the corresponding channel of the tube.

The presence of a check valve in one of the lines prevents liquid leakage from the mixing chamber into the corresponding container, thereby ensuring proper delivery of the liquid contained in the latter.

By providing each delivery line with a check valve, it is therefore possible to prevent liquid leakage from the mixing chamber into each container, thereby ensuring proper delivery of the various treatment liquids.

Consequently, when the pressure in the mixing chamber is greater than that of one of the containers, due to for example the connecting of gravity infusions and positive pressure infusions (of the push syringe type) to the housing of the delivery device, the liquid contained in the mixing chamber cannot leak out into this container thanks to the presence of a check valve disposed in the delivery line corresponding to this container.

Advantageously, the delivery lines of the housing converge towards the center of the housing in an area having a diameter corresponding substantially to that of the tube, wherein each line has an outlet orifice orientated perpendicularly to the plane in which the lines are disposed, wherein each orifice is facing a channel of the tube.

Preferably, each outlet orifice is extended by a hollow pin engaged into the corresponding channel of the tube.

According to one embodiment of the invention, the housing is of a circular shape, and the tube is connected axially to the housing.

According to another embodiment of the invention, the tube comprises a central channel and parallel and peripheral channels.

Advantageously, one of the lines of the housing comprises two outlet orifices, facing the central channel and one peripheral channel respectively.

Preferably, the tube is flared at the proximal end thereof.

According to another embodiment of the invention, the housing includes a cylindrical sleeve intended to receive, by force-fitting, the proximal end of the tube.

Advantageously, each line of the housing is closed at the outer wall of the housing by means of an occluder that can be pierced, is slit or has a moving valve device.

Preferably, each line of the housing delimits, at its inwardly turned end, a seat in which a Luer type tubular end piece is mounted thereby forming a connection means for the corresponding container and is used for housing the corresponding occluder.

According to another feature of the invention, each line delimits a chamber in which a plunger is mounted mobile in translation thereby forming a check valve, wherein the plunger is mobile between a first position enabling the passage of liquid from the corresponding container into the corresponding channel of the tube and a second position preventing the passage of liquid from the corresponding channel into the corresponding container.

Advantageously, each occluder is tubular and has a first closed end and a second open end, and each plunger is arranged so as to occlude the open end of the corresponding occluder when it is in its second position.

Preferably, each plunger has a thin end intended to occlude the open end of the corresponding occluder when the plunger is in its second position.

Advantageously, the thin end of each plunger is frustro-conical.

According to one embodiment the invention, each plunger has a diameter corresponding to the diameter of the corresponding chamber, and each plunger includes at least one longitudinal groove provided on its outer surface and intended to allow the passage of liquid from the corresponding container to the corresponding channel of the tube.

Preferably, the delivery device comprises a substantially cylindrical base on which the housing is mounted, wherein the base forms a winding drum for the tube.

Advantageously, the delivery device comprises sensors mounted on the outer side of the housing, wherein each sensor is intended to measure at least one characteristic value of the flow of liquid in the delivery line.

In any case, the invention will be clearly understood from the following description, in reference to the appended schematic drawing representing, as a non-limiting example, a preferred embodiment of the delivery device according to the invention.

Figure 1:
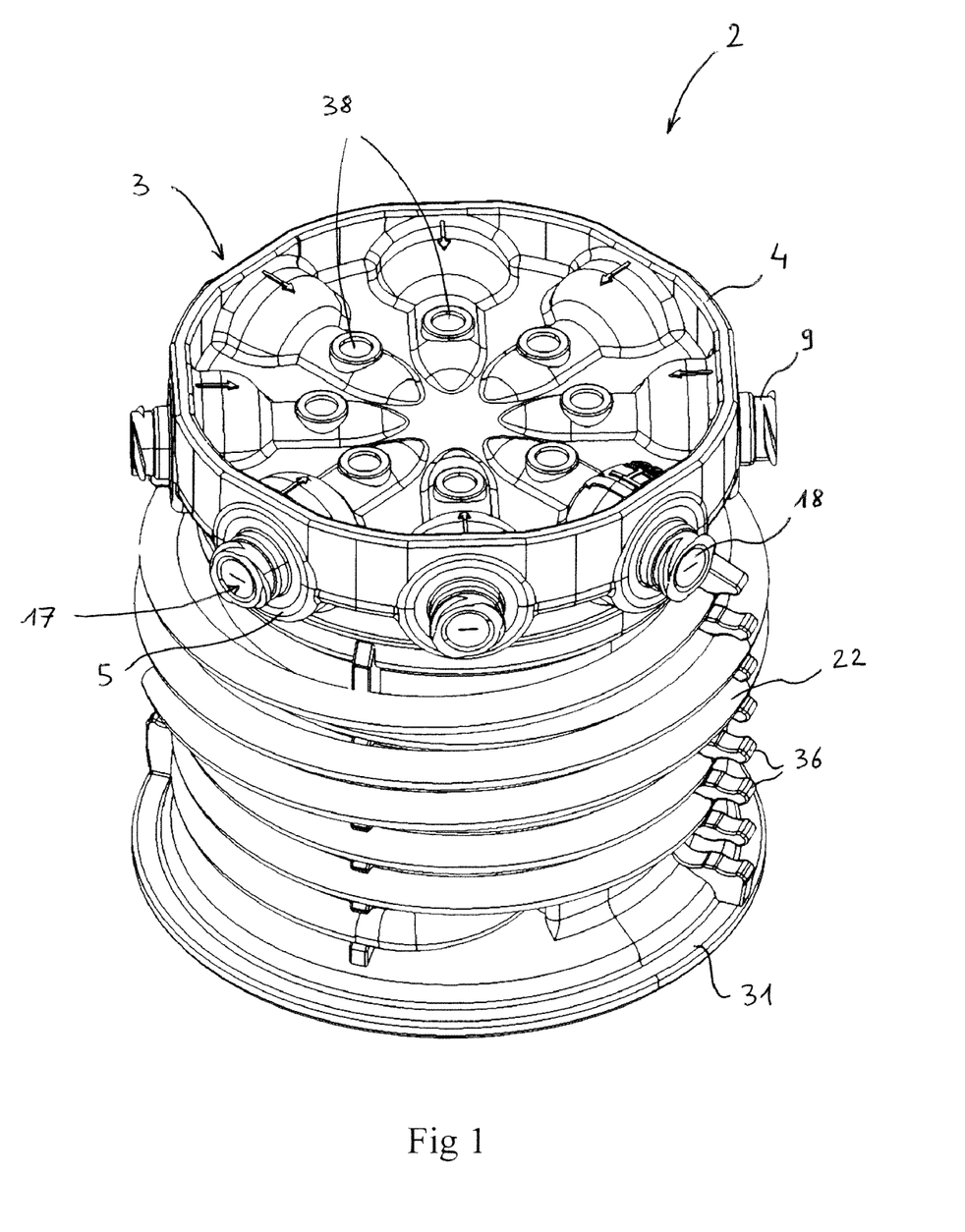
FIG. 1 is a perspective view.
Figure 2:
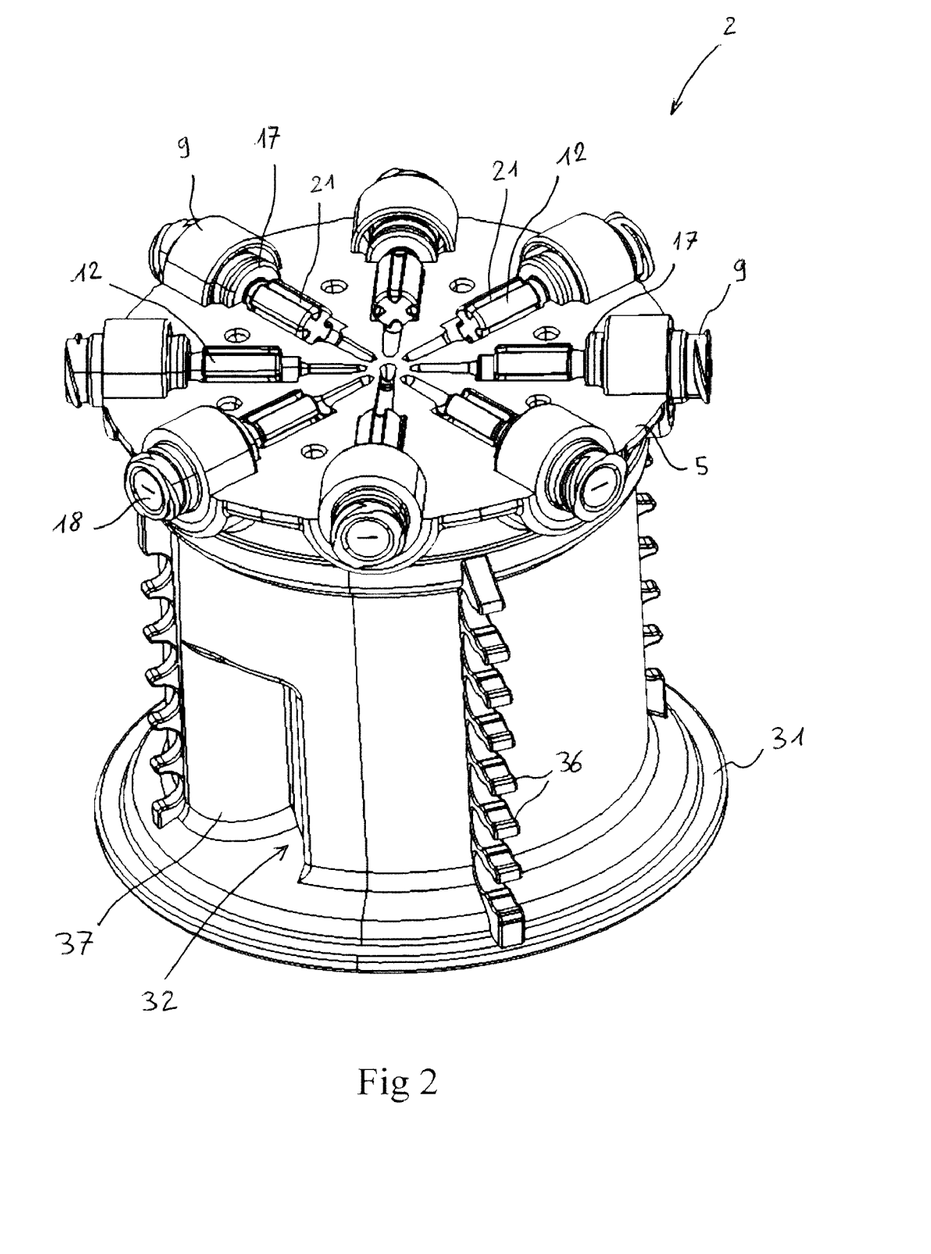
FIG. 2 is a perspective view in which the upper flask of the housing has been removed.
Figure 3:
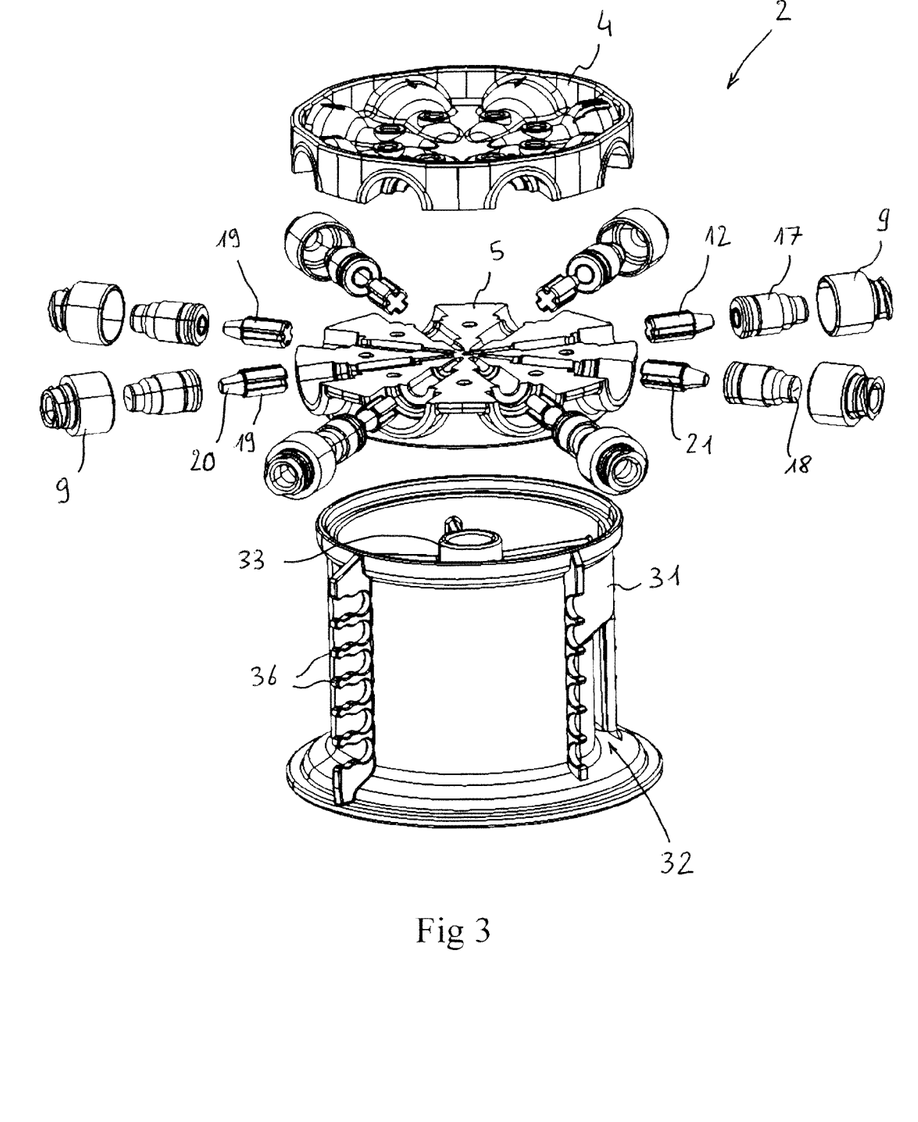
FIG. 3 is a perspective exploded view.
Figure 4:
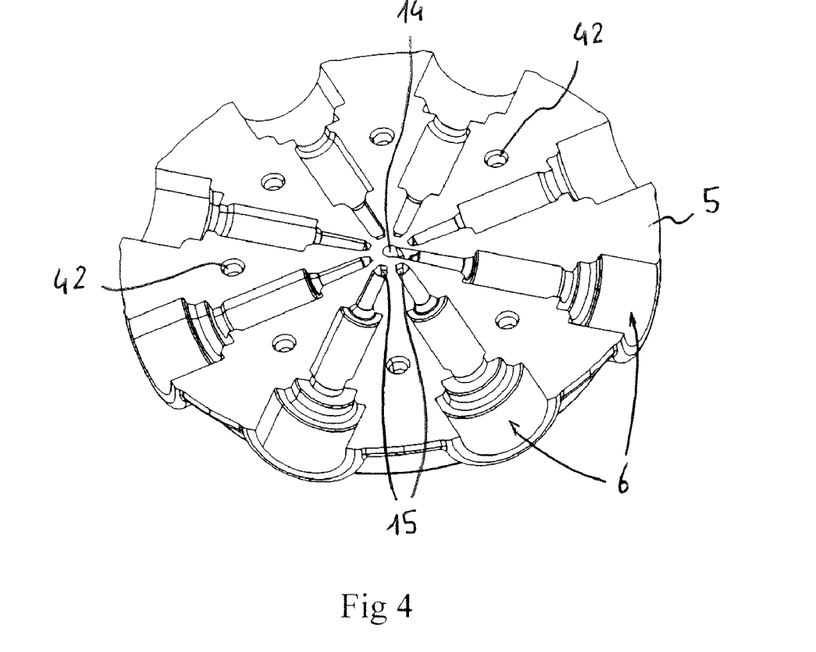
FIG. 4 is a perspective top view of the lower flask of the housing.
Figure 5:
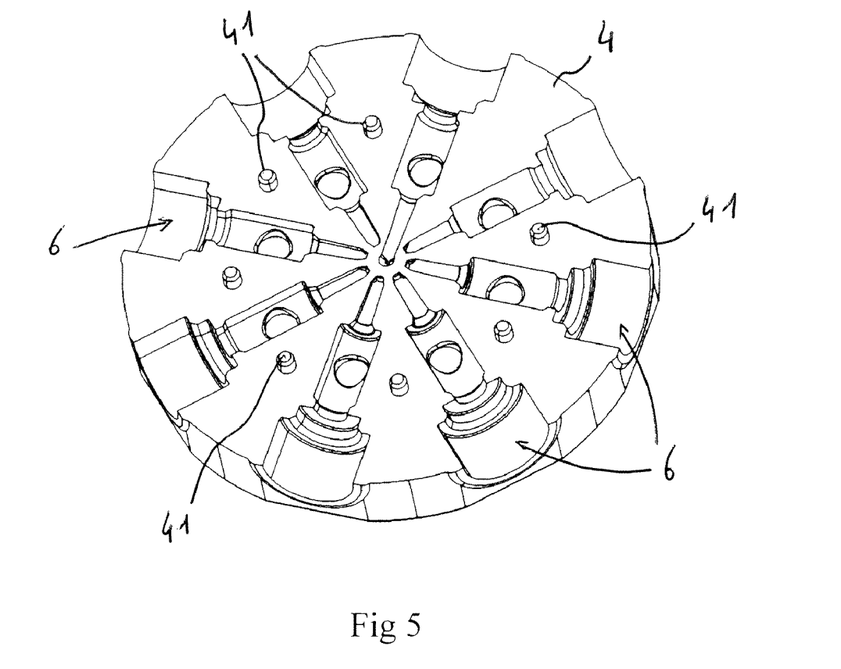
FIG. 5 is a perspective bottom view of the upper flask of the housing.

FIGS. 1 to 3 represent a delivery device 2 for delivering several medical treatment liquids to a human or animal patient.

The delivery device 2 comprises a housing 3 consisting of a circular upper flask 4 and a circular lower flask 5. The two flasks 4, 5 each comprise additional cavities 6 for forming liquid delivery lines 7 extending radially from the exterior of the housing 3 to the center of the housing.

The delivery lines 7 are spaced regularly. As shown more particularly in FIGS. 8 and 9, each delivery line 7 delimits, from the exterior towards the interior, a cylindrical seat 8 in which a Luer type tubular end piece 9 is mounted intended to be connected to a container containing a liquid, a cylindrical chamber 11 in which a plunger 12 is mounted mobile in translation thereby forming a check valve, and wherein a delivery channel 13 converges towards the center of the housing 3.

Figure 6:
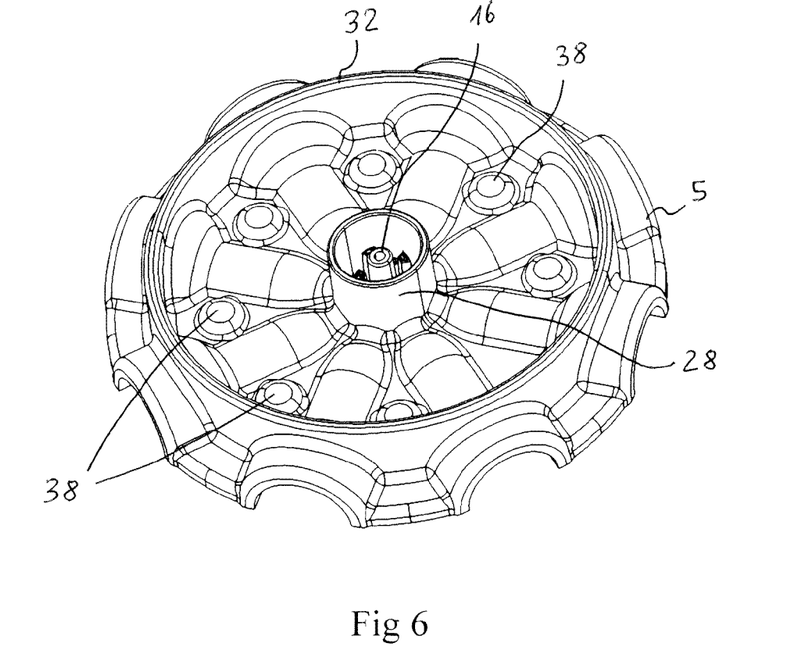
FIG. 6 is a perspective bottom view of the lower flask of the housing.
Figure 7:
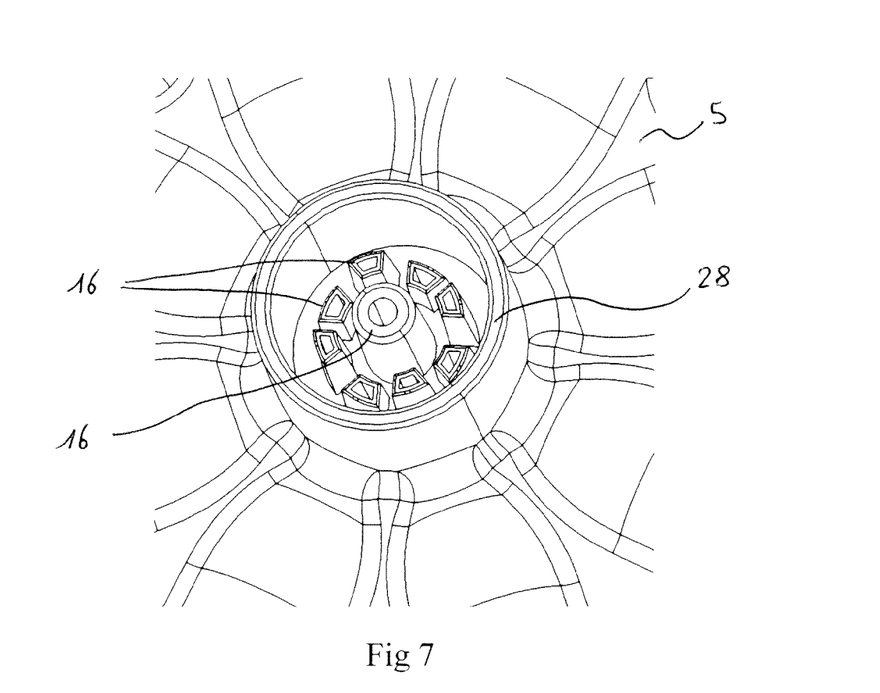
FIG. 7 is an enlarged scale view of the element of FIG. 6.

The lower flask 5 comprises parallel outlet orifices 14, 15 orientated perpendicularly to the plane in which the delivery lines 7 are disposed. The lower flask 5 comprises a central outlet orifice 14 and peripheral outlet orifices 15.

The delivery channel 13 of each delivery line 7 is extended by means of a peripheral outlet orifice 15 provided in the flask 5 whereas one of the delivery channels 13 is also extended by means of the central outlet orifice 14 such that the corresponding delivery line 7 comprises two outlet orifices.

Each outlet orifice 14, 15 is extended by a hollow pin 16 joined to the lower flask 5 and orientated perpendicularly to the plane in which the delivery lines 7 are disposed.

Each delivery line 7 is closed at the outer wall of the housing 3 by means of an occluder 17 housed in the corresponding end piece 9. Each occluder 17 is tubular and has a first outwardly turned end closed by a slit membrane 18 and a second inwardly turned open end.

Each plunger 12 comprises a first portion 19 substantially cylindrical having a diameter corresponding to that of the corresponding chamber 11, and a second frustroconical portion 20 turned towards the corresponding occluder 16.

Each plunger 12 includes longitudinal grooves 21 provided on the outer surface of its first portion 19 and intended to enable the passage of liquid coming from the corresponding container into the corresponding delivery channel 13.

Figure 8:
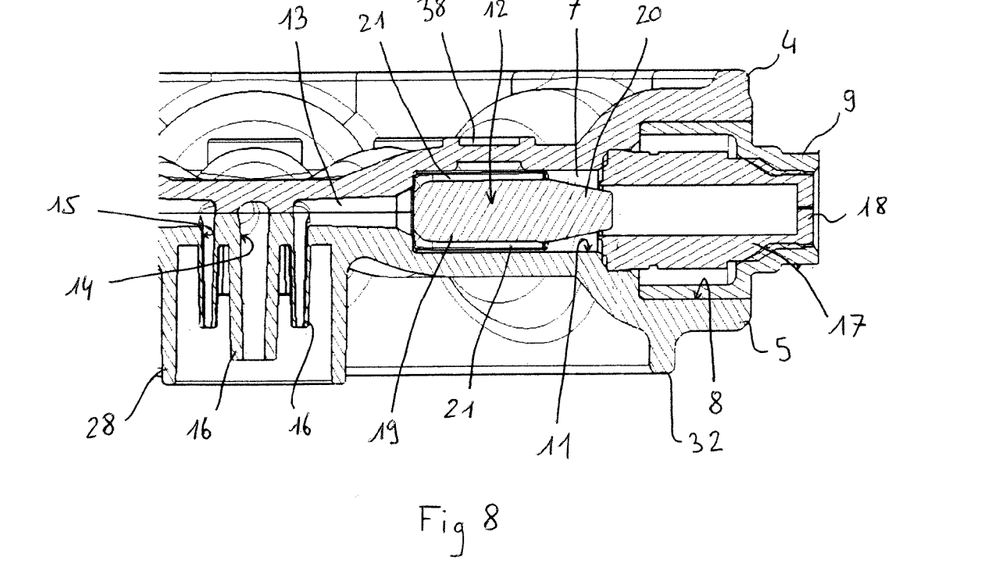
FIGS. 8 and 9 are partial cross-sectional views of the housing showing a plunger of a delivery line in two functioning positions.
Figure 9:
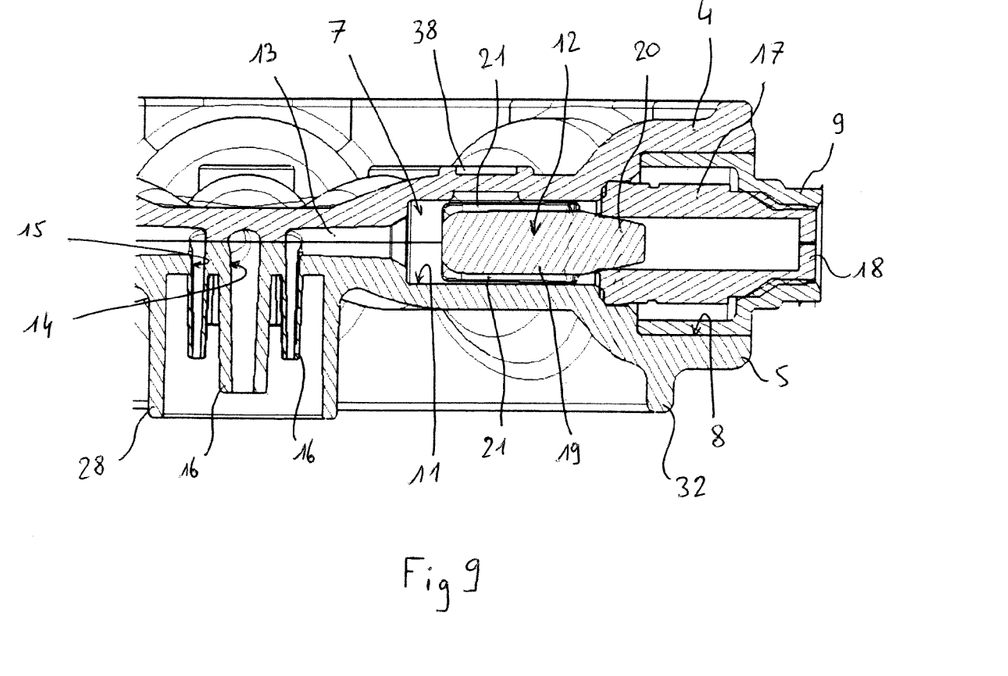

Each plunger 12 is mobile between a first position in which the frustroconical portion 20 of the plunger is situated at a distance from the open end of the corresponding occluder 16 and enables the passage of liquid from the corresponding container into the corresponding channel passage 13 and a second plunger in which the frustroconical portion 20 of the plunger occludes the open end of the corresponding occluder 17 and prevents the passage of liquid from the corresponding delivery channel 13 into the corresponding container.

The delivery device 2 further comprises a flexible tube 22 containing several channels 30 substantially parallel extending along the entire length of the tube. The proximal end of the tube is connected to the housing 3 whereas the distal end of the tube is connected with a connection element to the patient, thereby forming a mixing chamber for the various liquids coming from the containers connected to the housing 3.

Figure 11:
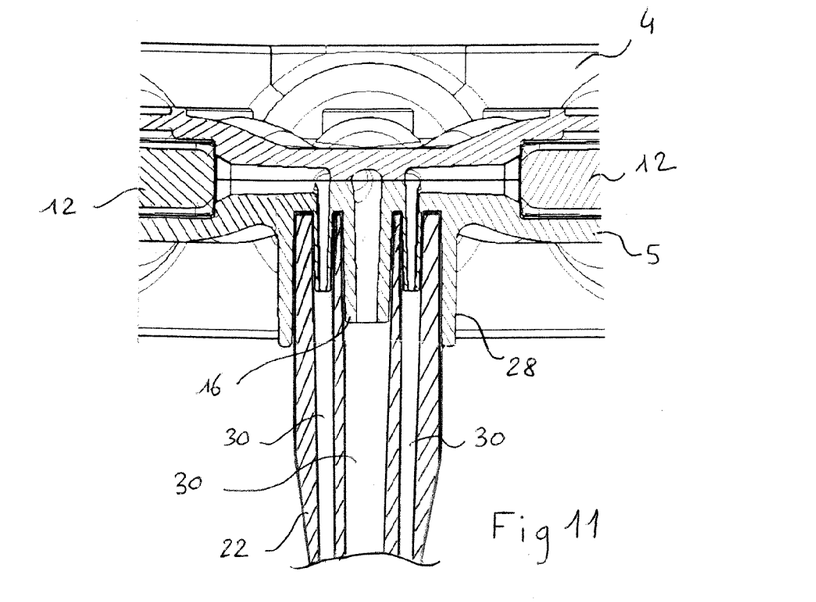
FIG. 11 is a partial cross-sectional view of the housing showing the connection between the housing and the tube.

The housing 3 includes an axial cylindrical sleeve 28 intended to receive, by force-fitting, the proximal end of the tube 22, wherein the tube is flared at the proximal end thereof so as to improve the fitting of the latter into the housing.

The tube 22 comprises a central channel into which the hollow pin 16 connected to the central outlet orifice 14 is engaged and parallel and peripheral channels into which the hollow pins 16 connected to the peripheral outlet orifices 15 are engaged respectively.

Thus, each delivery line 7 is intended to be connected to a container containing the liquid and to a channel of the tube 22 respectively.

It must also be noted that the delivery lines 7 of the housing 3 converge towards the center of the housing in an area having a diameter corresponding substantially to that of the tube 22.

Figure 10:
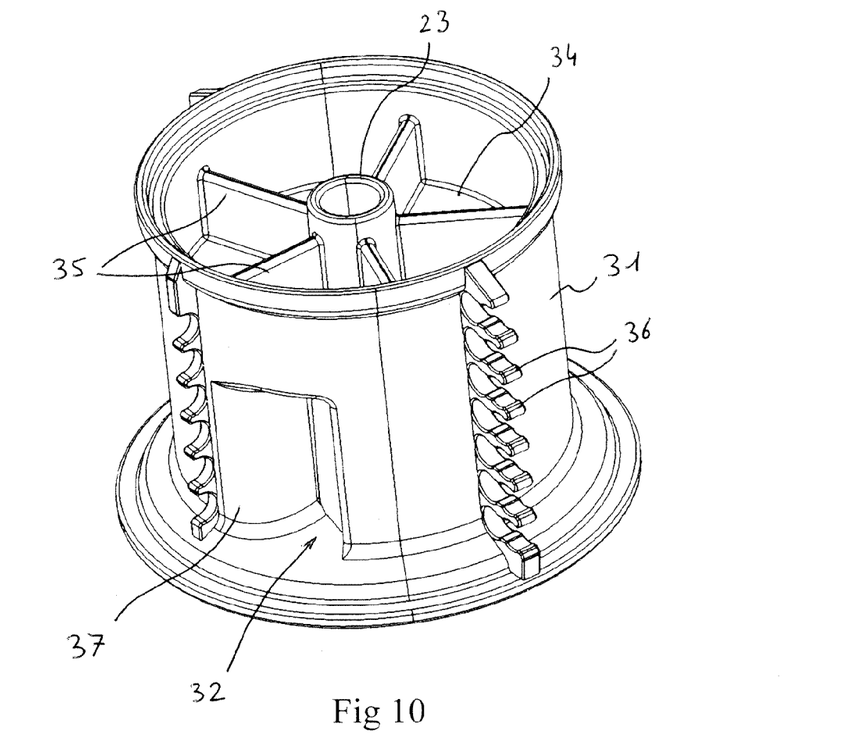
FIG. 10 is a perspective top view of the base.

The delivery device 2 further comprises a substantially cylindrical base 31 on which the housing 3 is mounted.

The housing 3 comprises an annular rib 32 provided on the lower side of the lower flask 5 and intended to cooperate with the inner surface of the base 31 so as to allow assembling of the housing and the base.

The base 31 comprises an axial guide socket 33 of the tube 22 connected to the inner lateral surface of the base by means of a circular crown 34 and connection tabs 35.

The base 31 also comprises a radial opening 32 intended to allow the passage of the tube 22.

The base 31 further includes, on its outer surface, hook tabs 36 thereby delimiting recesses for the tube and allowing the tube 22 to be wound twice around the base 31.

The base 31 thereby forms a winding drum for the tube 22. It must be noted that the base of the winding drum is widened in order to facilitate the occupancy thereof.

It must be noted that the opening 32 is delimited partially by a bent guiding portion 37 intended to prevent pinching of the tube 22 against the lateral wall of the base 31 when being wound around it.

According to one embodiment of the invention, the delivery device 2 could comprise sensors mounted on the outer side of the housing 3 in areas having had material removed 38, wherein each sensor is intended to measure one or more physical or chemical values characteristic of the flow of liquid in the delivery line.

According to another embodiment of the invention, each occluder 17 could be covered by a removable plug screwed onto the corresponding end piece 9.

The process for mounting and assembling the various components of the delivery device 2 will now be described.

This process for mounting and assembling comprises the following steps, consisting of:

positioning the occluders 17, the end pieces 9 and the plungers 12 in the corresponding cavities 6 provided in the lower flask 5, mounting the upper flask 4 onto the lower flask 5, wherein the mounting of the two flasks is facilitated by the presence of studs 41 and positioning recesses 42 provided in the upper 4 and lower 5 flasks respectively, joining the lower and upper flasks, by ultrasonic sealing for example, inserting the proximal end of the tube 22 into the radial opening 32 provided in the base 31 from the exterior towards the interior, then inserting it into the retaining socket 33, connecting, by force-fitting, the proximal end of the tube 22 into the sleeve 28 by engaging the pins 16 into the channels 30 of the tube 22.

mounting the housing 3 onto the base 31 by making the annular rib 32 cooperate with the inner surface of the base, winding the portion of tube 22, protruding from the opening 32, around the base by means of the hook tabs 36.

The functioning of the delivery device 2 will now be described.

Firstly, the user attaches the connection element that forms the mixing chamber to the patient, then connects the various containers, containing the medical treatment liquids to be delivered to the patient, to the Luer type end pieces $9^1$. It must be noted that each container, at its end connected to the corresponding end piece 9, comprises a liquid distribution portion intended to penetrate through the slit of the membrane 18 of the corresponding occluder 17.

The liquid contained in each container thus flows into the corresponding occluder 17, then along the longitudinal grooves 21 provided on the corresponding plunger 12, then into the corresponding delivery channel 13, into the corresponding channel of the tube 22 by means of the corresponding pin 16, and finally into the mixing chamber in order to be delivered to the patient.

When the differences in pressure between the venous pressure and the pressures present in the various containers trigger a displacement of liquid from the mixing chamber into one of the channels of the tube, the corresponding plunger 12 is thus displaced into its occluding position for the open end of the corresponding occluder 17, thereby preventing the passage of liquid from the mixing chamber into the corresponding container, and thus preventing the various liquids from mixing in this container.

It must be noted that the removal of each container connected to a Luer type end piece 9 triggers pressure reduction in the corresponding delivery lines 7, upstream from the corresponding plunger 12. This pressure reduction triggers a displacement of the plunger 12 into its occluding position for the open end of the corresponding occluder 17, thereby preventing the backflow of liquid from the mixing chamber into the corresponding delivery channel 13.

Thus, the presence of a plunger 12 in each delivery line 7 prevents, upon removal of a container connected to the housing 3, backflow of liquid from the mixing chamber into the corresponding delivery channel 13.

It is to be understood that the invention is not limited to the one specific embodiment of this delivery device, described above for merely exemplary purposes; it encompasses all of the variations of embodiment.

The invention claimed is:

1. Delivery device for delivering several medical treatment liquids to a human or animal patient, comprising a flexible tube containing several substantially parallel channels extending along the entire length of the tube of which one end, referred to as distal, is capable of being connected with a connection element to the patient, thereby forming a mixing chamber for the various liquids, and of which the other end, referred to as proximal, is connected to a housing provided with connection means for several containers each containing a liquid, wherein the housing has liquid delivery lines, wherein each delivery line is intended to be connected to a container and to a channel of the tube respectively, wherein at least one delivery line of the housing is provided with a check valve intended to enable the passage of liquid from only the corresponding container into the corresponding channel of the tube.

2. Delivery device according to claim 1, wherein the delivery lines of the housing converge towards the center of the housing in an area having a diameter corresponding substantially to that of the tube, wherein each line has an outlet orifice orientated perpendicularly to the plane in which the lines are disposed, wherein each orifice is facing a channel of the tube.

3. Delivery device according to claim 2, wherein each outlet orifice is extended by a hollow pin engaged into the channel of the corresponding tube.

4. Delivery device according to claim 1, wherein the housing is of a circular shape, and that the tube is connected axially to the housing.

5. Delivery device according to claim 1, wherein the tube comprises a central channel and parallel and peripheral channels.

6. Delivery device according to claim 5, wherein one of the lines of the housing comprises two outlet orifices, facing the central channel and a peripheral channel respectively.

7. Delivery device according to claim 1, wherein the tube is flared at the proximal end thereof.

8. Delivery device according to claim 1, wherein the housing includes a cylindrical sleeve intended to received, by force-fitting, the proximal end of the tube.

9. Delivery device according to claim 1, wherein each line of the housing is closed at the outer wall of the housing by means of an occluder that can be pierced, is slit or has a moving valve device.

10. Delivery device according to claim 9, wherein each line of the housing delimits, at its inwardly turned end, a seat in which a Luer type tubular end piece is mounted thereby forming a connection means for the corresponding container and is used for housing the corresponding occluder.

11. Delivery device according to claim 1, wherein each line delimits a chamber in which a plunger is mounted mobile in translation thereby forming a check valve, wherein the plunger is mobile between a first position enabling the passage of liquid from the corresponding container into the corresponding channel of the tube and a second position preventing the passage of liquid from the corresponding channel of the tube into the corresponding container.

12. Delivery device according to claim 9, wherein each occluder is tubular and has a first closed end and a second open end, and in that each plunger is intended to occlude the open end of the corresponding occluder when it is in its second position.

13. Delivery device according to claim 12, wherein each plunger has a thin end intended to occlude the open end of the corresponding occluder when the plunger is in its second position.

14. Delivery device according to claim 13, wherein the thin end of each plunger is frustroconical.

15. Delivery device according to claim 11, wherein each plunger has a diameter corresponding to the diameter of the corresponding chamber, and in that each plunger includes at least one longitudinal groove provided on its outer surface and intended to allow the passage of liquid from the corresponding container into the corresponding channel of the tube.

16. Delivery device according to claim 1, further comprising a substantially cylindrical base on which the housing is mounted, wherein the base forms a winding drum for the tube.

17. Delivery device according to claim 1, further comprising sensors mounted on the outer side of the housing, wherein each sensor is intended to measure at least one value characteristic of the flow of liquid in a delivery line.

* * * * *